United States Patent [19]

Nestor, Jr. et al.

[11] Patent Number: 5,696,103
[45] Date of Patent: Dec. 9, 1997

[54] METHOD FOR TREATING OSTEOPOROSIS

[75] Inventors: John Joseph Nestor, Jr., Cupertino; Brian Henry Vickery, Mountain View, both of Calif.; Milan Radoje Uskokovic, Upper Montclair, N.J.

[73] Assignees: Syntex (U.S.A.) Inc., Palo Alto, Calif.; Hoffmann-La Roche Inc., Nutley, N.J.

[21] Appl. No.: 560,080

[22] Filed: Nov. 17, 1995

[51] Int. Cl.$^6$ .................................................. A61K 31/59
[52] U.S. Cl. ............................................ 514/167; 514/168
[58] Field of Search ..................................... 514/167, 168

[56] References Cited

U.S. PATENT DOCUMENTS

| | | | |
|---|---|---|---|
| 4,804,502 | 2/1989 | Baggiolini et al. | 514/167 |
| 4,833,125 | 5/1989 | Neer, et al. | 514/12 |
| 4,853,378 | 8/1989 | Hamma et al. | 514/167 |
| 5,098,899 | 3/1992 | Gilbert et al. | 514/167 |
| 5,384,314 | 1/1995 | Doran | 514/167 |
| 5,512,554 | 4/1996 | Baggiolini | 514/167 |
| 5,622,941 | 4/1997 | Knutson | 514/167 |

FOREIGN PATENT DOCUMENTS

| | | |
|---|---|---|
| 0 205 025 | 12/1986 | European Pat. Off. . |
| 0 278 732 A1 | 8/1988 | European Pat. Off. . |
| 0 580 968 A2 | 2/1994 | European Pat. Off. . |
| WO 93/09093 | 5/1993 | WIPO . |

OTHER PUBLICATIONS

Kobayashi, Chem.Pharm. Bull., vol. 36(10), pp. 4144–4147, 1988.

Dechant, K., "Calcitriol –A Review of its Use in the Treatment of Postmenopausal Osteoporosis and its Potential in Corticosteroid–Induced Osteoporosis", *Drugs & Aging* 5(4):300–317, 1994.

Shiuey, S., "Total Synthesis of 1a–Fluoro–25–hydroxycholecalciferol and –ergocalciferol", *J. Org. Chem.* . vol. 55, No. 1, 243–247, 1990.

Okano, Toshio, Biochemical and Biophysical Research Comunications, vol. 163, No. 3, pp. 1444–1449, 1989.

*Primary Examiner*—C. Warren Ivy
*Assistant Examiner*—D. Margaret M. Mach
*Attorney, Agent, or Firm*—Heller Ehrman White & McAuliffe

[57] ABSTRACT

A method for treating osteoporosis via administration of a compound of the formula, 1α-fluoro-25-hydroxy-16-ene-23-yne-26,27-hexafluorocholecalciferol, in an amount therapeutically effective to restore bone density to an asymptomatic level, without inducing hypercalciuria, hypercalcemia, or nephrotoxicity is provided.

20 Claims, No Drawings

METHOD FOR TREATING OSTEOPOROSIS

BACKGROUND OF THE INVENTION a) Field of the Invention

This invention relates to a method for treating osteoporosis with an analog of Vitamin D.

b) Description of Related Art

Osteoporosis is the most common form of metabolic bone disease and may be considered the symptomatic, fracture stage of bone loss (osteopenia). Although osteoporosis may occur secondary to a number of underlying diseases, 90% of all cases appear to be idiopathic. Postmenopausal women are at risk for idiopathic osteoporosis (postmenopausal or Type I osteoporosis); another particularly high risk group for idiopathic osteoporosis is the elderly of either sex (senile or Type II osteoporosis). Osteoporosis has also been related to corticosteroid use, immobilization or extended bed rest, alcoholism, diabetes, gonadotoxic chemotherapy, hyperprolactinemia, anorexia nervosa, primary and secondary amenorrhea, transplant immunosuppression, and oophorectomy. Postmenopausal osteoporosis is characterized by fractures of the spine, while femoral neck fractures are the dominant features of senile osteoporosis.

The mechanism by which bone is lost in osteoporotics is believed to involve an imbalance in the process by which the skeleton renews itself. This process has been termed bone remodeling. It occurs in a series of discrete pockets of activity. These pockets appear spontaneously within the bone matrix on a given bone surface as a site of bone resorption. Osteoclasts (bone dissolving or resorbing cells) are responsible for the resorption of a portion of bone of generally constant dimension. This resorption process is followed by the appearance of osteoblasts (bone forming cells) which then refill with new bone the cavity left by the osteoclasts.

In a healthy adult subject, osteoclasts and osteoblasts function so that bone formation and bone resorption are in balance. However, in osteoporotics an imbalance in the bone remodeling process develops which results in bone being replaced at a slower rate than it is being lost. Although this imbalance occurs to some extent in most individuals as they age, it is much more severe and occurs at a younger age in postmenopausal osteoporotics, following oophorectomy, or in iatrogenic situations such as those resulting from corticosteroid therapy or the immunosuppression practiced in organ transplantation.

Various approaches have been suggested for increasing bone mass in humans afflicted with osteoporosis, including administration of androgens, fluoride salts, and parathyroid hormone and modified versions of parathyroid hormone. It has also been suggested that bisphosphonates, calcitonin, calcium, 1,25-dihydroxy vitamin $D_3$, and/or estrogens, alone or in combination, may be useful for preserving existing bone mass.

Hefti et al., *Clinical Science*, 62:389 (1982), describe studies using a high calcium diet supplemented with either parathyroid hormone or 1,25-$(OH)_2$ vitamin $D_3$ using normal and osteoporotic adult rats. The authors report that, although these studies showed an increase of whole-body calcium and skeletal mass, there was no restoration of individual trabeculae lost during the development of osteoporosis. Endo et al., *Nature*, 286:262 (1980), discuss the use of metabolites of vitamin D in conjunction with parathyroid hormone (PTH) to stimulate bone formation in vitro. However, these treatments with PTH and 1,25-$(OH)_2$ vitamin $D_3$ were no more effective than PTH alone in stimulating re-calcification of bone.

Rader et al., *Calcified Tissue International*, 29(1):21 (1979), describe the treatment of thyroparathyroidectomized rats with dietary calcium and intraperitoneal injection of a parathyroid extract. Although this treatment stimulated 1,25-$(OH)_2$ vitamin $D_3$ production and effected a marked increase in bone mineralization, it was also found to produce bone resorption as evidenced by the appearance of cavities in the cortical bone. There was no effect on rates of bone formation, or bone matrix apposition. Wong et al., *Surgical Forum*, 30:100 (1979), teach the administration to thyroparathyroidectomized dogs of daily intramuscular parathyroid extract or oral 1,25-$(OH)_2$ vitamin $D_3$ simultaneously with thyroid replacement therapy. The effect of these treatments on absorption of dietary calcium is discussed in the context of parathyroidism although not in the context of osteoporosis.

Peacock et al., *Vitamin D Proceedings Workshop.*, E. Norman, Ed., p. 411 (1977), disclose the inhibition by calcitonin and steroid sex hormones of the resorptive effect of vitamin D metabolites and parathyroid hormone on mouse calvaria bone in tissue culture. Pechet et al., *American Journal of Medicine*, 43(5):696 (1967), teach that minimum levels of parathyroid hormone are necessary in order for vitamin D to exert its effects on bone resorption rather than bone formation. In Mahgoub et al., *Biochemical and Biophysical Research Communications*, 62:901 (1975), the authors state that active vitamin D metabolites (25-OH vitamin $D_3$ and 1,25-$(OH)_2$ vitamin $D_3$) potentiate the ability of parathyroid hormone to elevate the cyclic AMP levels of cultured rat fetal bone cells.

Vitamin $D_3$ is a critical element in the metabolism of calcium, promoting intestinal absorption of calcium and phosphorus, maintaining adequate serum levels of calcium and phosphorus, and stimulating flux of calcium into and out of bone. The D vitamins are hydroxylated in vivo, with the resulting 1α,25-dihydroxy metabolite being the active material. Animal studies with 1,25-$(OH)_2$ vitamin D have suggested bone anabolic activity. Aerssens et al. in *Calcif Tissue Int.* 55:443–450 (1994) reported upon the effect of 1α-hydroxy Vitamin $D_3$ on bone strength and composition in growing rats with and without corticosteroid treatment. However, human usage is restricted to antiresorption due to the poor therapeutic ratio (hypercalciuria and hypercalcemia as well as nephrotoxicity).

Dechant and Goa, in "Calcitriol. A review of its use in the treatment of postmenopausal osteoporosis and its potential in corticosteroid-induced osteoporosis", *Drugs Aging* (NEW ZEALAND) 5(4):300–17 (1994), reported that 1,25-dihydroxyvitamin $D_3$ (calcitriol) has shown efficacy in the treatment of postmenopausal osteoporosis (and promise in corticosteroid-induced osteoporosis) based upon a clinical trial in 622 women with postmenopausal osteoporosis. Patients with mild to moderate disease (but not those with more severe disease) who received calcitriol (0.25 microgram twice daily) had a significant 3-fold lower rate of new vertebral fractures after 3 years of treatment, compared with patients receiving elemental calcium 1000 mg/day. In patients commencing long term treatment with prednisone or prednisolone, calcitriol 0.5 to 1.0 micrograms/day plus calcium 1000 mg/day, administered with or without intranasal calcitonin 400 IU/day, prevented steroid-induced bone loss. Overall, calcitriol was well tolerated. At recommended dosages hypercalcaemia was infrequent and mild, generally responding to reductions in calcium intake and/or calcitriol dosage. The narrow therapeutic window of calcitriol required that its use be adequately supervised, with periodic monitoring of serum calcium and creatinine levels. This study clearly identifies the key limitation of calcitriol therapy as the close proximity of therapeutic and toxic doses.

Baggiolini et al. in European Patent Publication No. 580,968 disclose fluorinated vitamin $D_3$ analogs, including 1α-fluoro-25-hydroxy-16-ene-23-yne-26,27-hexafluorocholecalciferol, useful for the treatment of hyperproliferative disorders of the skin, for the treatment of cancer and leukemia, and for the treatment of sebaceous gland diseases. Use for the restoration of bone mass and/or density in osteoporosis is not suggested.

SUMMARY OF THE INVENTION

This invention provides a method for treating osteoporosis via administration of a compound of the formula, 1α-fluoro-25-hydroxy-16-ene-23-yne-26,27-hexafluorocholecalciferol, in an amount therapeutically effective to restore bone density to an asymptomatic level, without inducing hypercalciuria, hypercalcemia, or nephrotoxicity.

Also provided are methods of treating medical conditions characterized by a decrease in bone density, said conditions selected from postmenopausal osteoporosis, senile osteoporosis, corticosteroid induced osteoporosis, immunosuppressive agent induced osteoporosis, osteodystrophy associated with hyperparathyroidism, and renal osteodystrophy, said methods comprising the administration of a compound of the formula 1α-fluoro-25-hydroxy-16-ene-23-yne-26,27-hexafluorocholecalciferol in an amount effective to restore bone density to an asymptomatic level, without inducing hypercalciuria, hypercalcemia, or nephrotoxicity.

DETAILED DESCRIPTION OF THE INVENTION

The compound of this invention may be prepared as taught by Baggiolini et al. in Example 3 of EP 580,968, as follows:

To a solution of 159 mg of [3S(3α,5β,Z)]-2-[2-[2-methylene-3-fluoro-5-[[(1,1-dimethylethyl)dimethylsilyl]-oxy]cyclohexylidene]ethyl]diphenyl phosphine oxide in 4.3 ml anhydrous tetrahydrofuran was added, at −75° C., 0.201 ml of 1.6M n-butyllithium in hexane under argon, until red color of the reaction mixture developed. After stirring for 6 min, a solution of 47 mg of [3aR-[1(R'),3aα,7aβ]]-3,3a,5,6,7,7a-hexahydro-7a-methyl-1-[6,6,6-trifluoro-5-hydroxy-1-methyl-5-(trifluoromethyl)-3-hexynyl]-4H-inden-4-one in 2.5 ml of anhydrous tetrahydrofuran was added dropwise. This reaction mixture was stirred in dark, and then quenched with a 1:1 mixture of 2N Rochelle salt and 2M $KECO_3$ at −75° C., and allowed to warm up to room temperature. It was diluted with 10.5 ml of the same salt mixture and extracted with ethyl acetate. The extract was washed with saturated brine, dried and evaporated. The crude product was purified by flash chromatography on silica gel with ethyl acetate-hexane 1:5 to give 27 mg of silyl protected 1α-fluoro-25-hydroxy-16-ene-23-yne-26,27-hexafluorocholecalciferol.

To a solution of 27 mg of the silyl intermediate in 1.8 ml anhydrous tetrahydrofuran was added 0.257 ml of 1M solution of tetrabutyl ammonium fluoride in tetrahydrofuran, and the reaction mixture was stirred at room temperature. It was then quenched with half-saturated $NaHCO_3$ and stirred at room temperature. The mixture was extracted with ethyl acetate, and the extract was washed with half-saturated $NaHCO_3$ and brine, dried and evaporated. The crude product was purified by flash chromatography with ethyl acetate-hexane 1:1.3 to give 19 mg of 1α-fluoro-25-hydroxy-16-ene-23-yne-26,27-hexafluorocholecalciferol as a glass; $[\alpha]_D^{25}$=+71.7° (c0.12,$CH_3OH$).

The compound of this invention is useful for the prevention and treatment of a variety of mammalian conditions manifested by loss of bone mass. In particular, the compound of this invention is indicated for the prophylaxis and therapeutic treatment of osteoporosis and osteopenia in mammals without inducing hypercalciuria, hypercalcemia, or nephrotoxocity. As used herein, "hypercalciuria" is excessive calcium in the urine, in humans corresponding to an excretion of greater than 4 mg/kg/day. This often results in nephrolithiasis (renal calculi). "Hypercalcemia" is an excessive concentration of calcium in the serum; in humans (and rats) this corresponds to greater than about 10.5 mg/dL. "Intolerable hypercalcemia", usually occurring at serum calcium concentrations greater than about 12 mg/dL, is associated with emotional lability, confusion, delirium, psychosis, stupor, and coma.

In general, the compound of this invention may be administered in amounts between about 0.0002 and 0.5 µg compound/kg body weight per day, preferably from about 0.001 to about 0.1 µg/kg body weight per day, most preferably from about 0.002 to about 0.02 µg/kg body weight per day. For a 50 kg human subject, the daily dose of active ingredient may be from about 0.01 to about 25 µgs, preferably from about 0.05 to about 5 µgs, most preferably from about 0.1 µg to about 1 µg per day. In other mammals, such as horses, dogs, and cattle, other doses may be required. This dosage may be delivered in a conventional pharmaceutical composition by a single administration, by multiple applications, or via controlled release, as needed to achieve the most effective results, preferably once daily by mouth. In certain situations, alternate day dosing may prove adequate to achieve the desired therapeutic response.

The selection of the exact dose and composition and the most appropriate delivery regimen will be influenced by, inter alia, the pharmacological properties of the formulation, the nature and severity of the condition being treated, and the physical condition and mental acuity of the recipient. In the treatment of corticosteroid induced osteopenia, it is expected that the requisite dose will be greater for higher doses of corticosteroids.

Representative delivery regimens include oral, parenteral (including subcutaneous, intramuscular and intravenous), rectal, buccal (including sublingual), pulmonary, transdermal, and intranasal, most preferably oral.

A further aspect of the present invention relates to pharmaceutical compositions comprising as an active ingredient the compound of the present invention, in admixture with a pharmaceutically acceptable, non-toxic carrier. As mentioned above, such compositions may be prepared for parenteral (subcutaneous, intramuscular or intravenous) administration, particularly in the form of liquid solutions or suspensions; for oral or buccal administration, particularly in the form of tablets or capsules; for pulmonary or intranasal administration, particularly in the form of powders, nasal drops or aerosols; and for rectal or transdermal administration.

The compositions may conveniently be administered in unit dosage form and may be prepared by any of the methods well-known in the pharmaceutical art, for example as described in *Remington's Pharmaceutical Sciences*, 17th ed., Mack Publishing Company, Easton, Pa., (1985). Formulations for parenteral administration may contain as excipients sterile water or saline, alkylene glycols such as propylene glycol, polyalkylene glycols such as polyethylene glycol, oils of vegetable origin, hydrogenated naphthalenes and the like. Formulations for nasal administration may be solid and may contain excipients, for example, lactose or dextran, or may be aqueous or oily solutions for use in the form of nasal drops or metered spray. For buccal administration typical excipients include sugars, calcium stearate, magnesium stearate, pregelatinated starch, and the like.

Orally administrable compositions may comprise one or more physiologically compatible carriers and/or excipients and may be in solid or liquid form, including, for example, tablets, coated tablets, capsules, lozenges, aqueous or oily suspensions, solutions, emulsions, elixirs, and powders suitable for reconstitution with water or another suitable liquid vehicle before use. Tablets and capsules may be prepared with binding agents, for example, syrup, acacia, gelatin, sorbitol, tragacanth, or polyvinylpyrollidone; fillers, such as lactose, sucrose, corn starch, calcium phosphate, sorbitol, or glycine; lubricants, such as magnesium stearate, talc, polyethylene glycol, or silica; and surfactants, such as sodium lauryl sulfate. Liquid compositions may contain conventional additives such as suspending agents, for example sorbitol syrup, methyl cellulose, sugar syrup, gelatin, carboxymethylcellulose, or edible fats; emulsifying agents such as lecithin, or acacia; vegetable oils such as almond oil, coconut oil, cod liver oil, or peanut oil; preservatives such as butylated hydroxyanisole (BHA) and butylated hydroxytoluene (BHT). Liquid compositions may be encapsulated in, for example, gelatin to provide a unit dosage form.

This invention is expected to be useful in the treatment of Type I (postmenopausal), Type II (senile), and Type III (iatrogenic) osteoporosis, including that associated with immunosuppressive drugs used in organ transplantation, as well in the treatment of osteodystrophy due to renal dialysis and hyperparathyroidism.

The following Examples are presented for illustrative purposes only.

EXAMPLE 1

BONE ANABOLISM IN THE RAT

This Example demonstrates that the test compound is more effective than 1,25-dihydroxy vitamin $D_3$ at bone accretion and does not induce hypercalciuria, nephrotoxicity, or hypercalcemia at therapeutically effective doses.

Three month old rats were ovariectomized and administered either 1,25-dihydroxy vitamin $D_3$ (1,25-di(OH)) or 1α-fluoro-25-hydroxy-16-ene-23-yne-26,27-hexafluorocholecalciferol (1αF) test compound once a day by mouth for a period of 3 weeks starting at 3 weeks post-ovariectomy and continuing until final sacrifice at 6 weeks post-ovariectomy. Blood was drawn at 4 weeks post-ovariectomy and again at the 6 week mark. Urine samples were taken and final femoral calcium determined upon sacrifice 6 weeks post-ovariectomy.

Femoral calcium was measured on the excised right femur. The femurs were cut in half, calcium extracted from the distal half femur (DHF), measured with a Calcette® calcium analyzer, and expressed as mean bone calcium in mg/DHF.

The compounds (1,25-di(OH) and 1αF) were evaluated at 0.05, 0.1, and 0.2 μg/kg/day. The results are summarized in Table 1. At the completion of the test period (6 weeks), sham operated controls displayed femoral calcium of 41.2 mg/femur; ovariectomized rats 39.0 mg/femur. Rats treated with 1,25-dihydroxy vitamin $D_3$ showed statistically insignificant improvements in femur calcium levels relative to OVX controls after treatment with the three doses. At all three dose levels, hypercalciuria was observed, and, at the highest dose, intolerable hypercalcemia as well. Following treatment with the test compound (1αF), statistically significant improved femur calcium levels were obtained at the two higher doses without evidence of hypercalcemia. Only at the highest dose was there a marginal elevation in urinary calcium.

The markedly improved therapeutic ratio exhibited by the compound of this invention, as compared to that of 1,25-di(OH) vitamin $D_3$, is completely unexpected and may afford an opportunity of clinical significance.

TABLE 1

FEMORAL, SERUM, AND URINARY CALCIUM LEVELS
Mean (SEM)

|  | FEMORAL CALCIUM (MG/DHF) | SERUM CA[a] (MG/DL) | 19TH DAY URINARY CA[b] (MG, 0–4 HRS) |
|---|---|---|---|
| SHAM + VEHICLE | 41.2(1.2) | 9.93(0.07) | 0.46(0.12) |
| OVX + VEHICLE | 39.0(1.3) | 9.96(0.05) | 0.40(0.08) |
| OVX + 1,25-di(OH) | | | |
| 0.05 μg/kg | 41.6(1.1) | 9.97(0.13) | 1.11(0.18)[b] |
| 0.1 | 42.2(0.9) | 10.60(0.19)[a] | 1.63(0.35)[b] |
| 0.2 | 41.2(1.0) | 12.00(0.15)[a] | 2.62(0.33)[b] |
| OVX + 1αF | | | |
| 0.05 μg/kg | 39.8(1.1) | 10.27(0.18) | 0.60(0.15) |
| 0.1 | 42.9(1.3)[c] | 10.48(0.15) | 0.70(0.14) |
| 0.2 | 44.4(1.5)[c] | 10.28(0.15) | 1.24(0.30)[b] |

[a]Hypercalcemia >10.5 mg/dL; intolerable hypercalcemia >12 mg/dL
[b]Hypercalciuria >1.1 mg/4 hrs
[c]p-value <0.03 versus OVX control

EXAMPLE 2

ORAL DOSAGE FORM SOFT GELATIN CAPSULE

A capsule for oral administration is formulated under nitrogen in amber light from 0.01 to 25.0 μg of 1α-fluoro-25-hydroxy-16-ene-23-yne-26,27-hexafluorocholecalciferol in 150 mg of fractionated coconut oil, with 0.015 mg butylated hydroxytoluene (BHT) and 0.015 mg butylated hydroxyanisole (BHA), filled in a soft gelatin capsule.

The following claims set forth with specificity that which we consider to be our invention and should be construed as broadly as the nature of this invention warrants.

We claim:

1. A method for treating osteoporosis via administration of a compound of the formula, 1α-fluoro-25-hydroxy-16-ene-23-yne-26,27-hexafluorocholecalciferol, in an amount therapeutically effective to restore bone density to an asymptomatic level, without inducing hypercalciuria, hypercalcemia, or nephrotoxicity.

2. A method of claim 1 in which the therapeutically effective amount of compound is from about 0.0002 μg compound/kg body weight/day to about 0.5 μg compound/kg body weight/day.

3. A method of claim 1 in which the therapeutically effective amount of compound is from about 0.001 μg compound/kg body weight/day to about 0.1 µg compound/kg body weight/day.

4. A method of claim 1 in which the therapeutically effective amount of compound is from about 0.002 µg compound/kg body weight/day to about 0.02 µg compound/kg body weight/day.

5. A method of claim 1 in which the compound is delivered in unit dosage form.

6. A method of claim 5 in which the unit dosage is from about 0.01 to about 25 µgs/day.

7. A method of claim 5 in which the unit dosage is from about 0.05 to about 5 µgs/day.

8. A method of claim 5 in which the unit dosage is from about 0.1 to about 1 µgs/day.

9. A method of claim 1 in which the compound is administered orally.

10. A method of treating a medical condition characterized by a decrease in bone density, said condition selected from postmenopausal osteoporosis, senile osteoporosis, corticosteroid induced osteoporosis, immunosuppressive agent induced osteoporosis, osteodystrophy associated with hyperparathyroidism, and renal osteodystrophy, said method comprising the administration of a compound of the formula 1α-fluoro-25-hydroxy-16-ene-23-yne-26,27-hexafluorocholecalciferol in an amount effective to restore bone density to an asymptomatic level, without inducing hypercalciuria, hypercalcemia, or nephrotoxicity.

11. A method of claim 10 in which the condition to be treated is postmenopausal osteoporosis.

12. A method of claim 10 in which the condition to be treated is senile osteoporosis.

13. A method of claim 10 in which the condition to be treated is immunosuppressive agent induced osteoporosis.

14. A method of claim 10 in which the condition to be treated is renal osteodystrophy.

15. A method of claim 10 in which the condition to be treated is osteodystrophy associated with hyperparathyroidism.

16. A method of claim 10 in which the therapeutically effective amount of compound is from about 0.0002 µg compound/kg body weight/day to about 0.5 µg compound/kg body weight/day.

17. A method of claim 10 in which the therapeutically effective amount of compound is from about 0.001 µg compound/kg body weight/day to about 0.1 µg compound/kg body weight/day.

18. A method of claim 10 in which the therapeutically effective amount of compound is from about 0.002 µg compound/kg body weight/day to about 0.02 µg compound/kg body weight/day.

19. A method of claim 10 in which the compound is delivered in unit dosage form.

20. A method of claim 10 in which the compound is administered orally.

* * * * *